(12) United States Patent
Daily et al.

(10) Patent No.: US 11,291,351 B2
(45) Date of Patent: Apr. 5, 2022

(54) HYSTEROSCOPES WITH CURVED TIPS

(76) Inventors: Harold I. Daily, Houston, TX (US); Andy C. Yim, Houston, TX (US)

( * ) Notice: Subject to any disclaimer, the term of this patent is extended or adjusted under 35 U.S.C. 154(b) by 0 days.

(21) Appl. No.: 13/589,736

(22) Filed: Aug. 20, 2012

(65) Prior Publication Data

US 2013/0046139 A1 Feb. 21, 2013

Related U.S. Application Data

(60) Provisional application No. 61/525,414, filed on Aug. 19, 2011.

(51) Int. Cl.
| | | |
|---|---|---|
| *A61B 1/00* | (2006.01) | |
| *A61B 1/303* | (2006.01) | |
| *A61B 1/012* | (2006.01) | |
| *A61B 1/015* | (2006.01) | |
| *A61B 1/07* | (2006.01) | |

(52) U.S. Cl.
CPC ...... *A61B 1/00071* (2013.01); *A61B 1/00179* (2013.01); *A61B 1/00195* (2013.01); *A61B 1/012* (2013.01); *A61B 1/015* (2013.01); *A61B 1/07* (2013.01); *A61B 1/303* (2013.01)

(58) Field of Classification Search
CPC .................. A61F 6/225; A61B 17/435; A61B 2018/00559; A61B 17/32002; A61B 2017/320008; A61B 2017/320028; A61B 17/1671; A61B 5/01; A61B 1/0011; A61B 1/00167; A61B 1/07; A61B 1/307; A61B 1/00094; A61B 1/015; A61B 1/12; A61B 1/313; A61B 1/3132; A61B 1/317; A61B 1/005; A61B 1/008; A61B 1/01; A61B 1/00071; A61B 1/012; A61B 1/0051; A61B 1/0052; A61B 1/0053; A61B 1/0055; A61B 1/0056; A61B 1/0057; A61B 1/0058; A61B 1/00195; A61B 1/00163; A61B 1/00165; A61B 1/00179; A61B 1/00174; A61B 1/00177; A61B 1/303
USPC ................... 385/119; 359/799; 600/156, 164
See application file for complete search history.

(56) References Cited

U.S. PATENT DOCUMENTS

| | | | | |
|---|---|---|---|---|
| 3,297,022 A | * | 1/1967 | Wallace ............. | A61B 1/00195 356/241.5 |
| 3,677,262 A | * | 7/1972 | Zukowski .......... | A61B 1/00165 385/117 |
| 3,858,586 A | * | 1/1975 | Lessen ................... | A61B 17/42 606/49 |
| 4,557,255 A | * | 12/1985 | Goodman .............. | A61B 1/307 600/104 |
| 4,742,819 A | * | 5/1988 | George ............. | A61B 1/00052 348/73 |
| 4,779,612 A | * | 10/1988 | Kishi .................... | A61B 1/0051 600/137 |
| 4,802,461 A | * | 2/1989 | Cho ..................... | A61B 1/0051 600/108 |

(Continued)

*Primary Examiner* — Ryan N Henderson
(74) *Attorney, Agent, or Firm* — James R. Hayne, Esq.; Stites & Harbison PLLC

(57) ABSTRACT

A hysteroscope includes a shaft comprising a fiber optic light channel, an operating channel, and two fluid circulating channels; and a zero-angle lens disposed at an distal end of the fiber optic light channel, wherein a distal section of the shaft has a bent section, and wherein the bent section has a deflection angle of about 5-40 degrees relative to a longitudinal axis of the remaining section of the shaft.

22 Claims, 3 Drawing Sheets

(56) References Cited

U.S. PATENT DOCUMENTS

| | | | | |
|---|---|---|---|---|
| 4,911,148 A * | 3/1990 | Sosnowski | A61B 1/0051 | 600/136 |
| 4,934,340 A * | 6/1990 | Ebling | A61B 1/0058 | 600/117 |
| 5,083,549 A * | 1/1992 | Cho | A61B 1/00071 | 600/108 |
| 5,127,393 A * | 7/1992 | McFarlin | A61B 1/00154 | 600/114 |
| 5,147,353 A * | 9/1992 | Everett | A61B 18/24 | 128/831 |
| 5,199,417 A * | 4/1993 | Muller | A61B 1/07 | 600/128 |
| 5,290,294 A * | 3/1994 | Cox | A61B 1/307 | 600/104 |
| 5,303,719 A * | 4/1994 | Wilk | A61B 17/32002 | 128/831 |
| 5,307,803 A * | 5/1994 | Matsuura | A61B 1/0051 | 138/118 |
| 5,363,882 A * | 11/1994 | Chikama | A61B 1/0055 | 138/103 |
| 5,386,817 A * | 2/1995 | Jones | A61B 1/00091 | 138/108 |
| 5,406,938 A * | 4/1995 | Mersch | A61B 1/00096 | 353/20 |
| 5,463,712 A * | 10/1995 | Cawood | A61B 1/00181 | 385/117 |
| 5,476,090 A * | 12/1995 | Kishi | A61B 1/00135 | 600/121 |
| 5,512,034 A * | 4/1996 | Finn | A61B 1/00089 | 600/138 |
| 5,536,234 A * | 7/1996 | Newman | A61B 1/00091 | 600/104 |
| 5,647,840 A * | 7/1997 | D'Amelio | A61B 1/00091 | 600/169 |
| 5,672,171 A * | 9/1997 | Andrus | A61B 18/24 | 600/108 |
| 5,735,792 A * | 4/1998 | Vanden Hoek | A61B 1/00087 | 600/138 |
| 5,807,239 A * | 9/1998 | DiBernardo | A61B 1/00135 | 600/114 |
| 5,823,940 A * | 10/1998 | Newman | A61B 1/303 | 600/105 |
| 5,855,549 A * | 1/1999 | Newman | A61B 1/00091 | 600/135 |
| 5,876,330 A * | 3/1999 | Grabover | A61B 1/0011 | 600/129 |
| 5,921,917 A * | 7/1999 | Barthel | A61B 1/07 | 600/120 |
| 5,941,816 A * | 8/1999 | Barthel | A61M 16/0488 | 600/120 |
| 5,951,461 A * | 9/1999 | Nyo | A61B 1/2676 | 600/118 |
| 6,007,531 A * | 12/1999 | Snoke | A61B 1/0052 | 604/95.04 |
| 6,110,103 A * | 8/2000 | Donofrio | A61B 1/126 | 600/114 |
| 6,112,747 A * | 9/2000 | Jones | A61B 18/24 | 128/830 |
| 6,143,013 A * | 11/2000 | Samson | A61M 25/005 | 604/264 |
| 6,165,123 A * | 12/2000 | Thompson | A61B 1/00078 | 600/114 |
| 6,190,308 B1 * | 2/2001 | Irion | A61B 1/042 | 348/188 |
| 6,196,966 B1 * | 3/2001 | Kerin | A61B 1/0008 | 600/104 |
| 6,352,549 B1 * | 3/2002 | Everett | A61B 18/24 | 606/135 |
| 6,378,524 B1 * | 4/2002 | Jones | A61B 18/24 | 128/830 |
| 6,458,076 B1 * | 10/2002 | Pruitt | A61B 1/0051 | 600/128 |
| 6,599,237 B1 * | 7/2003 | Singh | A61B 1/0008 | 600/114 |
| 6,761,684 B1 * | 7/2004 | Speier | A61B 1/00142 | 600/121 |
| 6,814,698 B2 * | 11/2004 | Barthel | A61B 1/00165 | 600/129 |
| 6,832,986 B2 * | 12/2004 | Chhibber | A61B 1/042 | 600/120 |
| 7,033,314 B2 * | 4/2006 | Kamrava | A61B 1/07 | 600/104 |
| 7,699,773 B2 * | 4/2010 | Forkey | A61B 1/00096 | 600/133 |
| 7,934,504 B2 * | 5/2011 | Lowe | A61F 6/18 | 128/830 |
| 7,942,814 B2 * | 5/2011 | Remijan | A61B 1/00135 | 600/121 |
| 7,985,178 B2 * | 7/2011 | Dahmen | A61B 1/0011 | 600/130 |
| 8,206,349 B2 * | 6/2012 | Slenker | A61B 1/00091 | 604/109 |
| 8,221,311 B2 * | 7/2012 | Campos | A61B 1/0008 | 600/129 |
| 8,528,563 B2 * | 9/2013 | Gruber | 128/832 | |
| 8,556,851 B2 * | 10/2013 | Hirszowicz | A61M 25/0119 | 604/103.14 |
| 9,125,550 B2 * | 9/2015 | Shener-Irmakoglu | A61B 17/0218 | |
| 9,445,714 B2 * | 9/2016 | Vazales | A61M 16/0463 | |
| 2002/0042608 A1 * | 4/2002 | Beyar | A61B 18/18 | 606/15 |
| 2002/0173699 A1 * | 11/2002 | Becker | A61B 1/00135 | 600/114 |
| 2003/0004460 A1 * | 1/2003 | Bedell | A61M 25/0136 | 604/95.04 |
| 2003/0069473 A1 * | 4/2003 | Barthel | A61B 1/0051 | 600/139 |
| 2004/0073088 A1 * | 4/2004 | Friedman | A61B 1/00142 | 600/114 |
| 2004/0225187 A1 * | 11/2004 | Kamrava | A61B 1/303 | 600/139 |
| 2005/0049459 A1 * | 3/2005 | Hern | A61B 1/12 | 600/121 |
| 2005/0054900 A1 * | 3/2005 | Mawn | A61B 5/065 | 600/156 |
| 2005/0272975 A1 * | 12/2005 | McWeeney | A61B 1/00103 | 600/113 |
| 2005/0288551 A1 * | 12/2005 | Callister | A61B 17/12177 | 600/115 |
| 2006/0252993 A1 * | 11/2006 | Freed | A61M 25/0147 | 600/146 |
| 2007/0083217 A1 * | 4/2007 | Eversull | A61B 1/053 | 606/114 |
| 2007/0142709 A1 * | 6/2007 | Martone | A61B 1/0014 | 600/121 |
| 2008/0058595 A1 * | 3/2008 | Snoke | A61B 1/00135 | 600/114 |
| 2008/0071269 A1 * | 3/2008 | Hilario | A61B 17/42 | 606/50 |
| 2008/0076966 A1 * | 3/2008 | Isaacson | A61B 17/29 | 600/106 |
| 2008/0097292 A1 * | 4/2008 | Cabiri | A61M 25/0122 | 604/95.01 |
| 2008/0108869 A1 * | 5/2008 | Sanders et al. | 600/109 | |
| 2008/0146873 A1 * | 6/2008 | Adams | A61B 17/42 | 600/104 |
| 2008/0154256 A1 * | 6/2008 | Payne | A61B 18/1485 | 606/34 |
| 2008/0172033 A1 * | 7/2008 | Keith | A61B 1/018 | 604/506 |
| 2008/0214891 A1 * | 9/2008 | Slenker | A61B 1/00091 | 600/109 |
| 2008/0214895 A1 * | 9/2008 | Campos | A61B 1/00089 | 600/129 |
| 2008/0221391 A1 * | 9/2008 | Weitzner | A61B 1/00165 | 600/118 |

(56) References Cited

U.S. PATENT DOCUMENTS

| Publication No. | Date | Inventor | Classification | Subclass |
|---|---|---|---|---|
| 2009/0018397 A1* | 1/2009 | Scholly | A61B 1/128 | 600/178 |
| 2009/0069632 A1* | 3/2009 | McIntyre | A61B 1/00098 | 600/146 |
| 2009/0192350 A1* | 7/2009 | Mejia | A61B 1/042 | 600/109 |
| 2009/0270812 A1* | 10/2009 | Litscher | A61B 17/42 | 604/164.01 |
| 2009/0270896 A1* | 10/2009 | Sullivan | A61B 17/320016 | 606/170 |
| 2010/0298642 A1* | 11/2010 | Trusty | A61B 1/0057 | 600/114 |
| 2010/0298643 A1* | 11/2010 | Eisele | G02B 23/2476 | 600/162 |
| 2011/0060184 A1* | 3/2011 | Rothberg | A61B 1/00135 | 600/104 |
| 2011/0061659 A1* | 3/2011 | Cruzada | A61F 6/18 | 128/831 |
| 2011/0061660 A1* | 3/2011 | Cruzada | A61F 6/06 | 128/831 |
| 2011/0105850 A1* | 5/2011 | Voegele | A61B 17/3423 | 600/207 |
| 2011/0160715 A1* | 6/2011 | Ostrovsky | A61B 1/0125 | 606/28 |
| 2011/0295066 A1* | 12/2011 | Fan | A61B 1/015 | 600/114 |
| 2012/0010646 A1* | 1/2012 | Keith | A61B 1/01 | 606/196 |
| 2012/0022314 A1* | 1/2012 | Sing | A61N 5/1027 | 600/3 |
| 2012/0071716 A1* | 3/2012 | Fructus | A61B 1/00071 | 600/106 |
| 2012/0078038 A1* | 3/2012 | Sahney | A61B 1/303 | 600/104 |
| 2012/0238819 A1* | 9/2012 | Long | A61B 1/0052 | 600/149 |
| 2012/0253120 A1* | 10/2012 | Callister | A61B 1/00082 | 600/106 |
| 2012/0253125 A1* | 10/2012 | Slenker | A61B 1/0125 | 600/139 |
| 2012/0289858 A1* | 11/2012 | Ouyang | A61B 1/00124 | 600/562 |
| 2012/0310215 A1* | 12/2012 | Stout | A61B 17/42 | 604/528 |
| 2012/0316391 A1* | 12/2012 | Weitzner | A61B 17/00234 | 600/104 |
| 2012/0323069 A1* | 12/2012 | Stout | A61B 1/303 | 600/104 |
| 2013/0046139 A1* | 2/2013 | Daily | A61B 1/012 | 600/104 |
| 2013/0046316 A1* | 2/2013 | Sullivan | A61B 10/0275 | 606/115 |
| 2013/0103021 A1* | 4/2013 | Germain | A61B 1/1482 | 606/33 |
| 2013/0144125 A1* | 6/2013 | Konstorum | A61B 1/00066 | 600/131 |
| 2013/0211321 A1* | 8/2013 | Dubois | A61B 17/320708 | 604/26 |
| 2013/0231652 A1* | 9/2013 | Germain | A61B 18/18 | 606/33 |
| 2014/0066706 A1* | 3/2014 | McWeeney | A61B 1/00154 | 600/104 |
| 2014/0276207 A1* | 9/2014 | Ouyang | A61B 1/015 | 600/567 |
| 2014/0288460 A1* | 9/2014 | Ouyang | A61B 1/053 | 600/570 |
| 2015/0190172 A1* | 7/2015 | Eversull | A61B 1/3137 | 600/585 |
| 2016/0106309 A1* | 4/2016 | Begg | A61B 1/00071 | 600/160 |
| 2016/0287287 A1* | 10/2016 | Eversull | A61B 1/051 | |

* cited by examiner

HYSTEROSCOPES WITH CURVED TIPS

CROSS REFERENCE TO RELATED APPLICATIONS

This claims the benefits of U.S. Provisional Patent Application No. 61/525,414, filed on Aug. 19, 2011, the disclosure of which is incorporated by reference in its entirety.

BACKGROUND OF INVENTION

Field of the Invention

This invention relates to medical devices, particularly hysteroscopes.

Background Art

Hysteroscopy is a procedure to inspect the uterine cavity for the diagnosis of intrauterine pathology. The procedures may include surgical intervention (operative hysteroscopy). In performing hysteroscopy, an endoscope (a hysteroscope) is inserted through the cervix into the uterus. A hysteroscope carries optical fibers or light channels and inflow and outflow channels for insufflation of the uterine cavity. In addition, an operating channel may be included to allow scissors, graspers or biopsy instruments to be used to perform operations.

FIG. 1 shows an example of a conventional hysteroscope. As shown, a hysteroscope 100 includes a straight shaft 19, which houses optic fibers and various channels (not shown). The proximal part includes a light source connector 10, two fluid controls 14a and 14b, each of which is connected to a bilateral (on/off) valve 13.

The straight shaft 19 is designed for ease of insertion of the hysteroscope. In addition, the straight shaft also makes it easier to pass various equipment (e.g., scissors, graspers or biopsy instruments) through the operating channel to perform operative hysteroscopy. While a straight shaft 19 serves these purposes, this configuration is not ideal for operations that need to access side walls or the areas of a uterus in the region of the fallopian tubal ostium. For example, to access fallopian tube or to place an Essure® birth control device would require operation in the cornual regions of a uterus. To facilitate viewing these areas of a uterus, the distal end of the straight shaft of such a conventional hysteroscope may be equipped with a lens arranged at an angle relative to the longitudinal axis, typically 30 degrees.

SUMMARY OF THE INVENTION

One aspect of the invention relates to hysteroscopes. A hysteroscope in accordance with one embodiment of the invention includes a shaft comprising a fiber optic light channel, an operating channel, and two fluid circulating channels; and a zero-angle lens disposed at an distal end of the fiber optic light channel, wherein a distal section of the shaft has a bent section, and wherein the bent section has a deflection angle of about 5-40 degrees relative to a longitudinal axis of the remaining section of the shaft. The fiber optic light channel, the operating channel, and the two fluid circulating channels may be integral parts of the shaft.

In accordance with embodiments of the invention, the shaft has the outside diameter of about 4-7 mm and the length of a bout 200-250 mm, wherein the bent section is about 20-35 mm long, and the deflection angle is about 10-30 degrees.

In accordance with embodiments of the invention, a hysteroscope further includes a light source connector disposed at a base section in a peripheral direction substantially the same as a direction of the bent section.

Other aspects and advantages of the invention will be apparent from the following description and the appended claims.

DETAILED DESCRIPTION

Embodiments of the invention relate to hysteroscopes designed and constructed so that a physician can use these instruments safely and with minimal discomfort to the female patient, and be able to insert the scope through the vagina and cervix into the uterine cavity for therapeutic or diagnostic medical purposes with relative ease. Specifically, hysteroscopes in accordance with embodiments of the invention relate to a bent tip at the distal end to facilitate viewing and access side walls or conual areas of a uterus.

Figure 1:
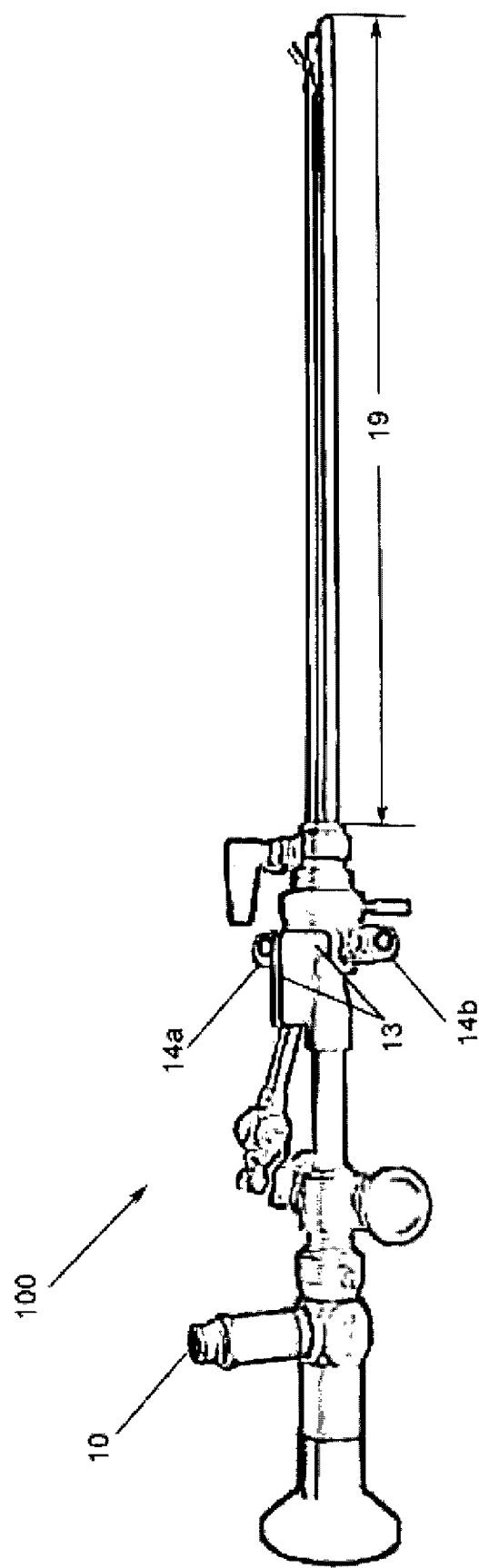
FIG. 1 shows a conventional hysteroscope.
Figure 2:
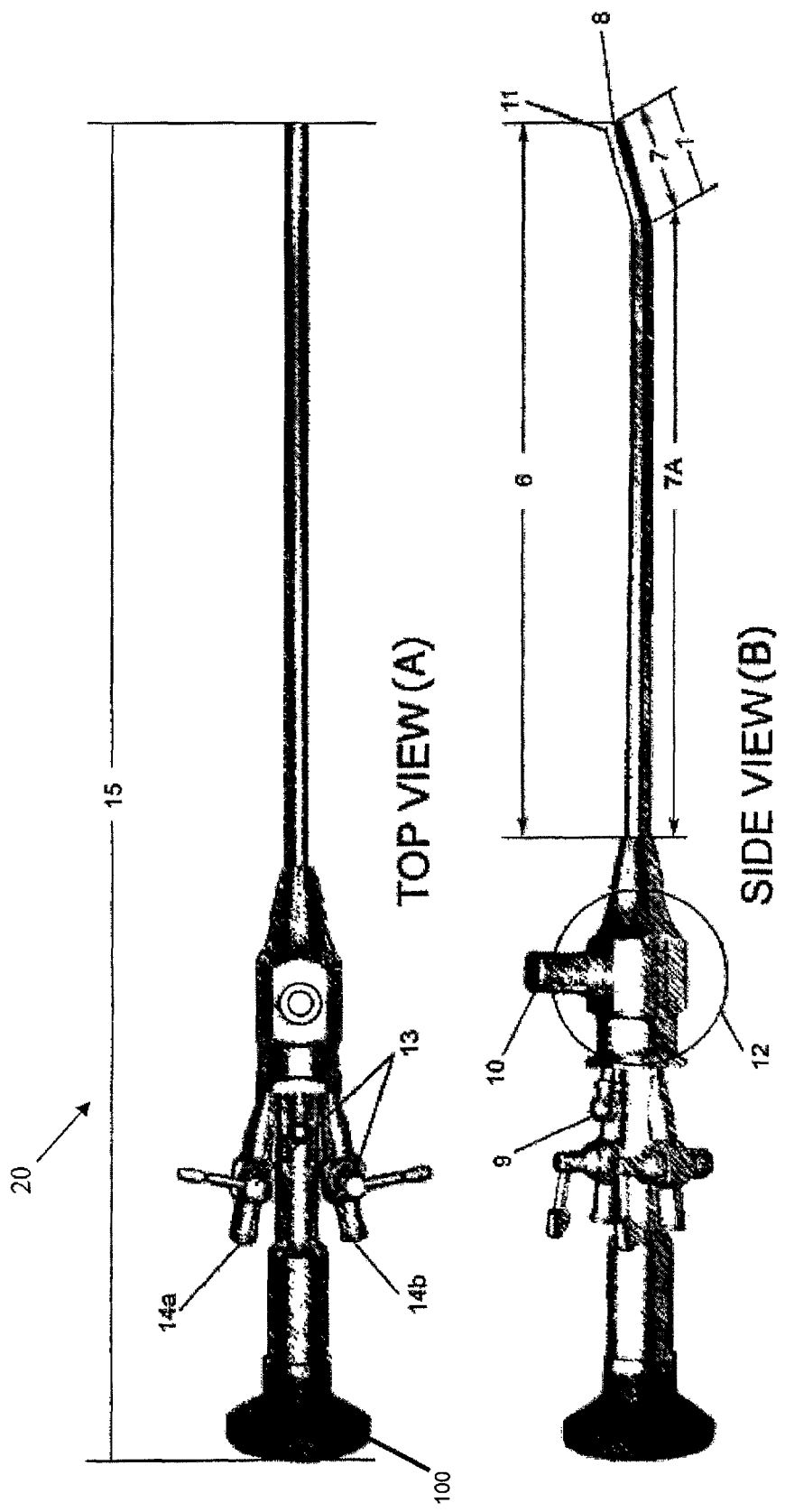
FIG. 2A shows a top view of a hysteroscope in accordance with one embodiment of the invention.
FIG. 2B shows a side view of the hysteroscope of FIG. 2A.

FIGS. 2A and 2B show one example of a hysteroscope in accordance with one embodiment of the invention. FIG. 2A shows a top view of a hysteroscope 20, while FIG. 2B shows its side view. As shown in FIG. 2B, the hysteroscope 20 may include conventional parts, such as fluid inlet and outlet 14a and 14b, bilateral (off and on) valves 13, a light source connector 10, an operating channel 9, and a shaft 11. The fluid inlet and outlet 14a and 14b are for fluid circulation to clear away debris and to allow uterine distention. In this example, the light source connector is located at the base region 12, which is also used for manipulating the hysteroscope shaft and tip in an up-and-down manner, to right or left, or in a circular manner, so as to obtain the direct view of the cervical canal or the inside of the expanded uterine body. While in this particular example, various components in the proximal region are shown to be at particular locations relative to each other, one skilled in the art would appreciate that other modifications and variations are possible without departing from the scope of the invention.

FIGS. 2A and 2B also including a viewing portion 100.

In accordance with embodiments of the invention, the shaft 11 includes a distal section 1 that is bent or curved such that the distal end 8 of the shaft is deflected from the main axis of the shaft (i.e., the longitudinal axis of the hysteroscope). In accordance with embodiments of the invention, the shaft 11 may have a length 6 of about 200-250 mm, preferably about 210-230 mm, more preferably about 220 mm. The bent section 1 may have a length 7 of about 10-50 mm, preferably about 20-35 mm, more preferably about 25-30 mm. This area where 7 and 7A meet allows for a suitable angle (e.g., 22 degrees) deflection of that portion of the hysteroscope shaft Please note that any numerical ranges disclosed in this description are intended to include all numbers therebetween, as if these numbers have been individually disclosed.

For example, in an exemplary hysteroscope of the invention, the shaft 11 may have a length of about 220 mm and the bent section 1 may have a length about 26 mm. This will leave the straight portion of the shaft having a length 7A of about 194 mm. Again, these specific numbers are for illustration only. One skilled in the art would appreciate that other dimensions are possible without departing from the scope of the invention.

Referring to FIG. 2B again, in accordance with embodiments of the invention, the light source connector 10 may be arranged in the same peripheral direction as the curve direction of the distal section 1, making it easier to know which way the distal end of the shaft 8 is pointed. It also allows for movement of the scope body and camera toward the opposite inner thigh position, from the scope tip and lens, in an unencumbered manner, so as to facilitate the head-on viewing of the fallopian tubal ostium.

However, in accordance with other embodiments of the invention, the peripheral directions of the light source connector 10 and the curved tip may not be aligned. Instead, the direction of the bend may be marked in some other manner, such as with a line or dot in the base section 12.

Figure 3:
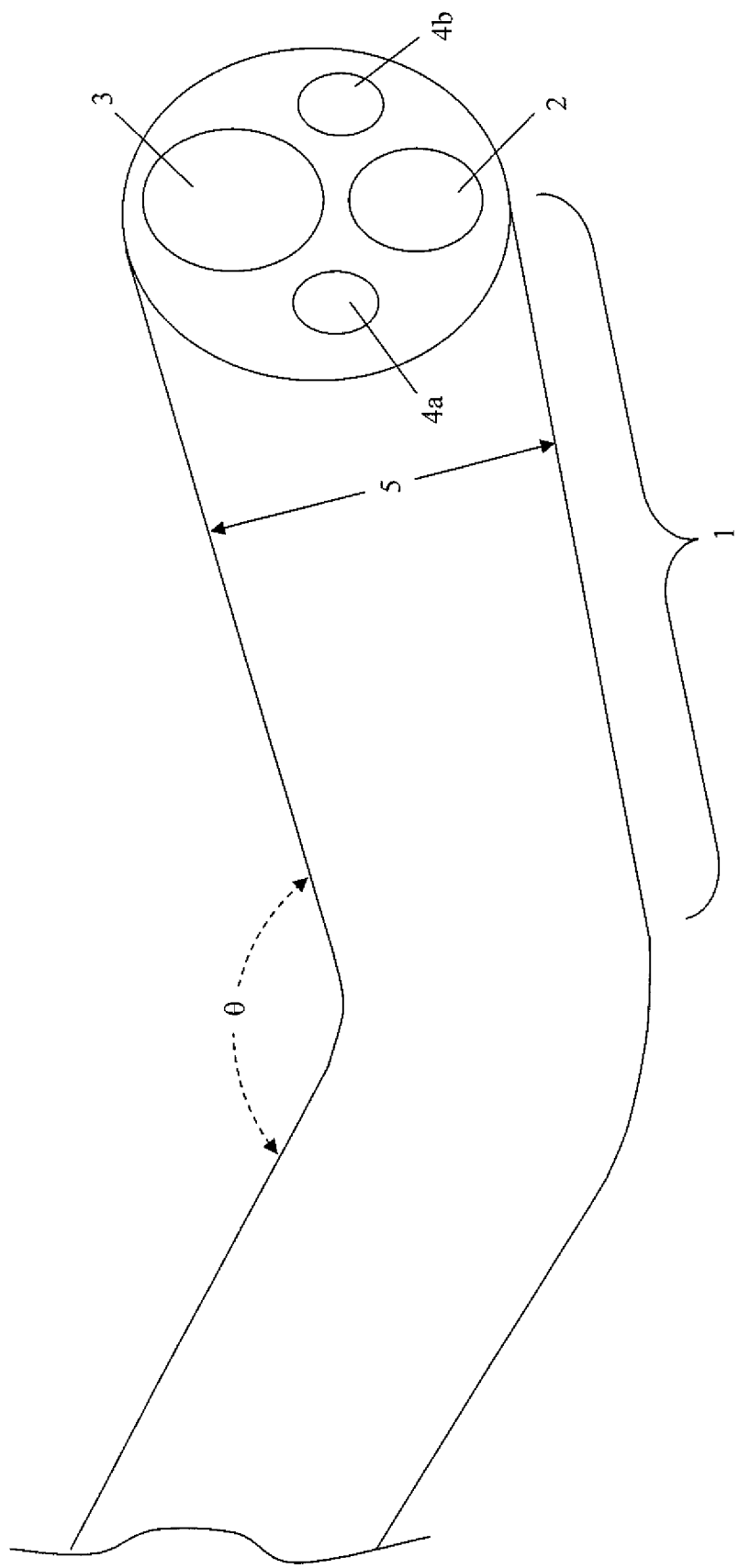
FIG. 3 shows a schematic illustrating detailed structure at the distal end of a hysteroscope in accordance with one embodiment of the invention.

FIG. 3 shows a schematic illustrating the curved distal section 1 of the shaft 11. This enlarged drawing illustrates various channels included in the shaft 11. For example, these channels may include a fiber optic light channel 2, an operating channel 3, and fluid circulation channels 4a and 4b (i.e., inflow and outflow channels). The shaft outside diameter 5 may be any suitable size, preferably in the range of about 3 mm to about 10 mm, more preferably about 4 mm to about 7 mm, and most preferably about 5 mm to about 6 mm. For example, the shaft outside diameter may be about 5.3 mm.

FIG. 3 also illustrates that the distal section 1 of the shaft is curved (or bent) from the main section of the shaft 11. The bend or curve allows one to use a zero-degree lens. A zero-degree lens forms a zero degree angle with respect to the tip end surface plane of the distal tip end 8 (see FIG. 2B). In other words, the zero-angle lens lies in a plane that is parallel with the end surface plane. The zero-angle lens allows the operator to have a head-on view of the viewable field and the fallopian tubal ostium when the Essure® procedure is being performed.

The angle θ of the bend or curve may be any suitable angle, for example in the range of from 5° to 40°, preferably from 10° to 30°, more preferably from 15° to 25°. For example, a hysteroscope of the invention may have a curve or bend angle θ of about 22°.

In accordance with some embodiments of the invention, the various channels in the shaft described above may be housed within a sheath (tubing) that is a separate piece. For example, all channels may be encased and kept in place (with a matrix) inside a stainless steel round tubing. In accordance with other embodiments of the invention, the various channels in the shaft may be made as integral parts of the shaft. In other words, the various channels may be machined in a solid piece of the material that comprises the shaft. The materials used for making the shaft and/or the channels may be any suitable materials used in medical devices. Examples of such materials include stainless steel, titanium, and polymers.

In accordance with embodiments of the invention, the composite small diameter shaft unit is durable, easy to clean and sterilize, and the encased design protects the delicate internal light fibers of the scope during transportation, utilization, and storage.

With a curved distal section, with a turn of the scope body either to the right or left, the uterine cavity cornual area with ostium (on that side) comes into view. A slight pressure of the scope body, toward the contra lateral side of the cervix and uterus, may allow a perfect 'head-on' view of the ostium and its attached fallopian tubes. As noted above, the light source connector may be located on the same side of the scope base as the direction of the deflection (bend) at the distal end of the shaft. This would help indicate the direction of the tip.

For example, with the scope shaft in place inside the uterine fundus and the scope light base connector in a lateral position and pointing in the same direction as the top of the deflected end of the shaft, the base may be now moved horizontally with slight pressure toward the patient's right or left inner thigh area. This will allow for a more lateral view inside the uterus, which now makes it possible to obtain a "head on" view of the right or left tubal ostium, especially when the tubal ostium is far lateral. The far lateral positioning of the tip of the scope shaft is often the difference in being able to insert a device (as the FDA approved Essure® Device) correctly through the ostium and into the proximal portion of the fallopian tube.

As shown in FIG. 2B, there are bilateral (off and on) valves 13, which are connected to the 2 fluid channels/tubes (4a & 4b) at their top ends (14a & 14b) of the unit for fluid control. Removal of small particles of mucous and blood from the region of the distal end of the shaft 8, during scope insertion or while viewing inside the uterine cavity may be accomplished by utilizing the 'wash effect' of fluid flowing out of the "outflow" channel.

The inflow channel 4a may be supplied with an adequate amount of fluid (usually physiological saline solution) through the inflow tube connector 14a and into the uterine cavity. Adequate distention and good viewing is obtained with a suitable flow rate, which may be accomplished by gravity with the fluid source at 1 to 2 feet about the cardiovascular level of the patient. This does not usually require increased pressure from a pressure pump or squeezing of the plastic fluid bag. Keeping the fluid source at the heart level will allow no greater than 155 mm Hg pressure inside the uterus. This would prevent damages caused by excessive pressure.

The second channel (outflow channel) 4b and outflow tube connector 14b, with its valve, can be used for outflow fluid circulation so that the blood and other debris can be removed from the uterine cavity, for example, during an active procedure of hysteroscopy. Leur lock connections may be equipped on the ends of the connectors 14a & 14b—one for a connection to the fluid source tubing that will be used for fluid inflow, and the other may be used along with rubber or plastic tubing to drain away the circulating fluid as the tip of the hysteroscope is introduced thru the cervix and while the distal end of the scope shaft (11 and 1) are in the uterine cavity.

The operating channel (9) may be any suitable size (typically about 2.4 mm) in diameter. In addition, it may be equipped with an external seal for introduction of a device, such as the Essure® device or can be used for other hysteroscopy instruments, such as scissors or forceps.

Advantages of the invention may include one or more of the following. A hysteroscope of the invention may have a unitary construction with a curved deflected distal end that permits the use of a zero-degree lens at the distal end of an optic channel. In contrast, conventional hysteroscope have straight shafts and tilted lens at the tips.

A conventional straight shaft hysteroscope normally compensates for the lack of peripheral vision, by making the optic lens with an angle. Physicians operating such a conventional scope would have to take this viewing angle into account when entering the cervical and uterine cavities. In contrast, a head-on scope with a zero degree lens, in accordance with embodiments of the invention, allows the user to naturally guide the scope without having to compensate for the angled lens. More importantly, a curved distal end with a head-on lens (zero degree lens) makes it ideal for procedures that require near "head on" viewing of the uterine fundal ostium (especially when the ostium is far lateral), such as the Essure® procedure.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What we claim is:

1. A hysteroscope, comprising:
   a shaft comprising:
      a fiber optic light channel,
      an operating channel, and
      two fluid circulating channels;
   wherein a distal section of the shaft has a bent section and at least a portion of a proximal end of the shaft includes a straight portion; and
   a base section including a viewing portion, a fluid inlet, a fluid outlet, and light source connector,
   wherein the shaft, including the distal section, is made of a unitary piece of stainless steel or titanium, and the shaft runs from the proximal end of the shaft, which connects with a base section of the hysteroscope, to a distal end of the shaft,
   wherein the bent section has a fixed deflection angle falling within a range of about 5-40 degrees relative to a longitudinal axis of the straight portion of the shaft,
   wherein the fiber optic light channel, the operating channel, and the two fluid circulating channels each have a central longitudinal axis parallel to and spaced a distance from a central longitudinal axis of the shaft,
   wherein the light source connector is provided spaced closer to the distal end than the fluid inlet, the fluid outlet and the viewing portion, and
   wherein the base section and the shaft are integrally formed.

2. The hysteroscope of claim 1, wherein the shaft has an outside diameter of about 4-7 mm and a length of about 200-250 mm, wherein the bent section is about 20-35 mm long, and the deflection angle is about 10-30 degrees.

3. The hysteroscope of claim 1, wherein the shaft has an outside diameter of about 5.3 mm and a length of about 220 mm, wherein the bent section is about 26 mm long, and the deflection angle is about 22 degrees.

4. The hysteroscope of claim 1, wherein the light source connector is disposed at the base region in a peripheral direction substantially the same as a direction of the bent section.

5. The hysteroscope of claim 1, wherein the fiber optic light channel, the operating channel, and the two fluid circulating channels are integral parts of the shaft.

6. The hysteroscope of claim 1, wherein the shaft has an outside diameter of about 4-7 mm and a length of about 200-250 mm, wherein the bent section is about 20-35 mm long, and the deflection angle is about 10-30 degrees.

7. The hysteroscope of claim 1, wherein the shaft has an outside diameter of about 5.3 mm and a length of about 220 mm, wherein the bent section is about 26 mm long, and the deflection angle is about 22 degrees.

8. The hysteroscope of claim 1, wherein the operating channel is configured for insertion of equipment therethrough.

9. The hysteroscope of claim 1, wherein the two fluid circulating channels are configured for fluid circulation to and from a body cavity.

10. A hysteroscope, comprising:
    a shaft made of a unitary piece of rigid material defining each of a fiber optic light channel, an operating channel, a fluid inlet circulating channel, and a fluid outlet circulating channel, and
    the shaft further including a straight section and a distal section that is a preformed bent section having a fixed deflection angle with respect to the straight section in a curve direction;
    a housing attached to the shaft, the housing defining a fluid inlet operably connected to the fluid inlet circulating channel and a fluid outlet operably connected to the fluid outlet circulating channel,
    a light source connector integrated with the housing, and
    a viewing portion attached to the housing and positioned further away from the distal end of the shaft than the light source connector,
    wherein each of the fiber optic light channel, the operating channel, the fluid inlet circulating channel, and the fluid outlet circulating channel have a central longitudinal axis parallel to and spaced a distance from a central longitudinal axis of the shaft.

11. The hysteroscope of claim 10, wherein the shaft has an outside diameter of about 4-7 mm and a length of about 200-250 mm, wherein the bent section is about 20-35 mm long, and the deflection angle is about 10-30 degrees.

12. The hysteroscope of claim 10, wherein the shaft has an outside diameter of about 5.3 mm and a length of about 220 mm, wherein the bent section is about 26 mm long, and the deflection angle is about 22 degrees.

13. The hysteroscope of claim 10, wherein the fiber optic light channel, the operating channel, the fluid inlet circulating channel, and the fluid outlet circulation channel are integral parts of the shaft.

14. The hysteroscope of claim 10, wherein the hysteroscope material is stainless steel or titanium.

15. The hysteroscope of claim 14, wherein the shaft has an outside diameter of about 4-7 mm and a length of about 200-250 mm, wherein the bent section is about 20-35 mm long, and the deflection angle is about 10-30 degrees.

16. The hysteroscope of claim 14, wherein the shaft has an outside diameter of about 5.3 mm and a length of about 220 mm, wherein the bent section is about 26 mm long, and the deflection angle is about 22 degrees.

17. The hysteroscope of claim 10, wherein the operating channel is configured for insertion of equipment therethrough.

18. A hysteroscope, comprising:
    a shaft having a proximal and a distal end, the shaft including:
       an operating channel,
       two fluid circulating channels, and
       a fiber optic channel,
    wherein the operating channel, the two fluid circulating channels, and the fiber optic channel each have a central axis parallel to a central longitudinal axis of the shaft and are integrally formed within the shaft between the proximal end and the distal end, the proximal end including a straight section and the distal end including a bent section having a fixed deflection angle with respect to the straight section;
    a housing attached to the shaft, the housing defining a fluid inlet and a fluid outlet;

a connector for the fiber optic channel, the connector integrated with the housing; and a viewing portion attached to the housing and positioned further away from the distal end of the shaft than the connector, wherein the connector is in communication with the fiber optic channel, and wherein the shaft is made of rigid material such that the fixed deflection angle of the bent section is maintained in the distal end of the shaft during insertion and manipulation of the shaft within a patient.

19. The hysteroscope of claim 18 further wherein the shaft has an outside diameter of 4-7 mm and a length of 200-250 mm, wherein the bent section is 20-35 mm long, and the deflection angle is 10-30 degrees.

20. The hysteroscope of claim 18 further wherein the fluid inlet and the fluid outlet are each in fluid communication with one of the two fluid circulating channels, respectively.

21. The hysteroscope of claim 10, wherein the housing and shaft are of unitary construction.

22. The hysteroscope of claim 18, wherein the connector is provided closer to the distal end of the shaft than the fluid inlet, the fluid outlet, and the viewing portion.

* * * * *